(12) United States Patent
Kellogg et al.

(10) Patent No.: US 8,067,186 B2
(45) Date of Patent: *Nov. 29, 2011

(54) MONOCLONAL ANTIBODY DS6, TUMOR-ASSOCIATED ANTIGEN CA6, AND METHODS OF USE THEREOF

(75) Inventors: Anne Elizabeth Kellogg, Ayden, NC (US); Diane A. Semer, Grimesland, NC (US)

(73) Assignee: East Carolina University, Greenville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/363,191

(22) Filed: Jan. 30, 2009

(65) Prior Publication Data

US 2009/0155930 A1    Jun. 18, 2009

Related U.S. Application Data

(60) Continuation of application No. 11/680,190, filed on Feb. 28, 2007, now Pat. No. 7,507,410, which is a division of application No. 10/465,176, filed on Jun. 19, 2003, now Pat. No. 7,351,805, which is a division of application No. 09/641,499, filed on Aug. 18, 2000, now Pat. No. 6,596,503.

(51) Int. Cl.
*G01N 33/53* (2006.01)
(52) U.S. Cl. .......................... 435/7.1; 435/325
(58) Field of Classification Search .................. None
See application file for complete search history.

(56) References Cited

U.S. PATENT DOCUMENTS

| | | | |
|---|---|---|---|
| 4,931,385 A * | 6/1990 | Block et al. | |
| 5,486,456 A | 1/1996 | Xu et al. | |
| 5,558,852 A | 9/1996 | Bigner et al. | |
| 5,624,659 A | 4/1997 | Bigner et al. | |
| 5,871,941 A | 2/1999 | Auersperg | |
| 2007/0041980 A1 | 2/2007 | Payne et al. | |

FOREIGN PATENT DOCUMENTS

WO    WO 2005/009369 A2    2/2005

OTHER PUBLICATIONS

Weiner et al. Sem. Oncology 26(4 Suppl 12):41-50, 1999.*
William E. Paul. Fundamental Immunology, 3rd ed., p. 242, 1993.*
Greenspan et al. (Nature Biotechnology. 1999; 7: 936-937).*
Stedman''s Medical Dictionary "epitope" http://www.stedmans.com, Sep. 30, 2009.*
Weiner et al (Sem. Oncology 1999;26(4 Suppl 12):41-50).
Kearse, Kelly P., et al., Monoclonal Antibody DS6 Detects a Tumor-Associated Sialoglycotope Expressed on Human Serous Ovarian Carcinomas, *Int. J. Cancer*, vol. 88, pp. 866-872 (2000).
Smith, et al., Immunohistochemically detecting target antigens in patient biopsies for tailoring monoclonal antibody based cancer therapy, *Human Antibodies*, vol. 9, pp. 61-65 (1999).
Smith, et al., Immunohistochemical Distribution of Tumor-Associated Antigen CA6 in Gynecological Neoplasms as Detected by Monoclonal Antibody DS6, *International Journal of Gynecological Pathology*, vol. 20, pp. 260-266 (2001).
International Search Report, International Application No. PCT/US01/41765, dated Feb. 13, 2002.
Seaver SS, Genetic Engineering News, Aug. 1994, 14 (14): 10 and 21.
Wennerberg, A.E. et al., "Target antigens for cancer therapy: Correlation with surgical pathology biopsies," oral presentation, Conference Program (Apr. 15, 1998), p. 15, Human Antibodies & Hybridomas '98 Conference, Washington, DC, plus confirmation letter from meeting organizer.
Devine et al. "Mucins: Structure, Function, and Associations with Malignancy", *BioEssays* 14(9):619-625 (1992).
Gendler et al. "Molecular Cloning and Expression of Human Tumor-associated Polymorphic Epithelial Mucin", *J. Bio. Chem.* 265(25):15286-15293 (1990).
Patton et al. "The epithelial mucin, MUC1, of milk, mammary gland and other tissues", *Biochimica et Biophysics Acta* 1241:407-424 (1995).
Chun et al. "Potent anti-cancer activity of DS6-DM1, an antibody drug conjugate targeting a Muc1 glycotope on ovarian, breast, and pancreatic carcinomas", *AACR-NCI-EORTC International Conference* (2003) (Powerpoint presentation).

* cited by examiner

*Primary Examiner* — Misook Yu
*Assistant Examiner* — Mark Halvorson
(74) *Attorney, Agent, or Firm* — Myers Bigel Sibley & Sajovec, PA

(57) ABSTRACT

The present application describes a monoclonal antibody selected from the group consisting of monoclonal antibody DS6, monoclonal antibodies that specifically bind to the antigen or epitope bound by monoclonal antibody DS6, and fragments of the foregoing that specifically bind to the antigen or epitope bound by monoclonal antibody DS6. Methods of use of such antibodies and the isolated antigen bound by such antibodies are also described.

11 Claims, 3 Drawing Sheets

MONOCLONAL ANTIBODY DS6, TUMOR-ASSOCIATED ANTIGEN CA6, AND METHODS OF USE THEREOF

RELATED APPLICATIONS

This application is a continuation application of U.S. patent application Ser. No. 11/680,190, filed Feb. 28, 2007, now U.S. Pat. No. 7,507,410, which is a divisional of U.S. patent application Ser. No. 10/465,176, filed Jun. 19, 2003, now issued U.S. Pat. No. 7,351,805, which is a divisional of U.S. patent application Ser. No. 09/641,499, now issued U.S. Pat. No. 6,596,503, filed Aug. 18, 2000. The disclosures of each of these applications are to be incorporated by reference herein in their entirety.

FIELD OF THE INVENTION

The present invention concerns the monoclonal antibody DS6, tumor-associated antigen CA6, and methods of use thereof.

BACKGROUND OF THE INVENTION

Malignancy-associated changes of tumor cell membrane sialoglycoproteins and sialoglycolipids (gangliosides) have been observed for decades and are implicated in many aspects of the transformed phenotype, including altered adhesive properties and metastatic potential (Bhavanandan, V. P., Furukawa, K., In: A. Rosenberg (ed.), *Biology of the Sialic Acids*, pp. 144-196, Plenum Press, New York (1995)). Altered, re-expressed or over-expressed sialoglycoconjugates, viewed as tumor-associated antigens (TAAs), are being investigated as targets for a variety of antibody-directed cancer therapies. Some examples include monoclonal antibodies (mabs) directed against sTn (TAG-72) in breast cancer therapy (Estava, F. J. and Hayes, D. F. Monoclonal antibody-based therapy of breast cancer. In: M. L. Grossbard (ed.), Monoclonal antibody-based therapy of cancer, pp. 309-338, Marcel Dekker, New York (1998)) and mabs to gangliosides such as GD2, GD3 and GM2 in the therapy of lung cancer and melanoma (Butler, M. O. and Haluska, F. G., In: M. L. Grossbard (ed.), *Monoclonal antibody-based therapy of cancer*, pp. 339-364, Marcel Dekker, New York (1998); Grant, S. C. et al., In: M. L. Grossbard (ed.), *Monoclonal antibody-based therapy of cancer*, pp. 365-395, Marcel Dekker, New York (1998)). Nevertheless, there remains a need for new ways to detect and treat cancer in patients.

SUMMARY OF THE INVENTION

The present invention is based upon the development of murine monoclonal antibody DS6 deposited in the American Type Culture Collection (ATCC), 10801 University Blvd., Manassas, Va., 20110-2209, on Jun. 11, 2002 and designated PTA-4449. This antibody immunohistochemically reacts with an antigen, CA6, that is expressed by human serous ovarian carcinomas but not expressed by normal ovarian surface epithelium or mesothelium. The CA6 antigen has a limited distribution in normal adult tissues and is most characteristically detected in fallopian tube epithelium, inner urothelium and type 2 pneumocytes. Pretreatment of tissue sections with either periodic acid or neuraminidase from *Vibrio cholerae* abolishes immunoreactivity with DS6 indicating that CA6 is a neuraminidase-sensitive and periodic acid-sensitive sialic acid glycoconjugate ("sialoglycotope"). SDS-polyacrylamide gel electrophoresis of OVCAR5 cell lysates reveals the DS6 epitope to be expressed on an 80 kiloDalton nondisulfide-linked glycoprotein containing N-linked oligosaccharides. Two-dimensional nonequilibrium pH gradient electrophoresis gels indicates an isoelectric point of approximately 6.2-6.5. DS6 immunostaining can be partially diminished by pretreatment of tissue sections with chloroform/methanol, suggesting that DS6 may also be expressed as a glycolipid. Comparison of the immunohistochemical distribution of the CA6 antigen in human serous ovarian adenocarcinomas reveals similarities to that of CA125, however, distinct differences and some complementarity of antigen expression are revealed by double-label, two-color immunohistochemical studies. The DS6-detected CA6 antigen appears distinct from other well-characterized tumor-associated antigens, including MUC1, CA125, and the histo-blood group-related antigens, sLea, sLex and sTn.

A first aspect of the present invention is a monoclonal antibody selected from the group consisting of monoclonal antibody DS6 and monoclonal antibodies that specifically bind to the antigen or epitope bound by monoclonal antibody DS6, and fragments of the foregoing that specifically bind to the antigen or epitope bound by monoclonal antibody DS6.

A second aspect of the present invention is a method of screening for the presence of cancer in a human subject, comprising the steps of: (a) contacting a biological sample taken from said subject with an antibody as described above under conditions permitting said antibody to specifically bind an antigen in the sample to form an antibody-antigen complex; and then (b) determining the amount of antibody-antigen complex in the sample as a measure of the amount of antigen in the sample, wherein an elevated level of the antigen in the sample is associated with the presence of cancer in said subject.

A further aspect of the present invention is a method of treating cancer in a subject in need thereof, comprising, administering to a subject afflicted with cancer a monoclonal antibody as described above in a therapeutically effective amount.

A still further aspect of the present invention is isolated tumor-associated antigen CA6, an about 80 kDa N-linked glycoprotein, reduced or non-reduced, with a PI of about 6.2-6.5, and containing a sialiadase and periodate sensitive epitope called DS6. Such antigen may be isolated by affinity purification with a monoclonal antibody DS6 as described herein.

The foregoing and other objects and aspects of the present invention are explained in detail in the drawings herein and the specification set forth below.

DETAILED DESCRIPTION OF THE PREFERRED EMBODIMENTS

Figure 1:
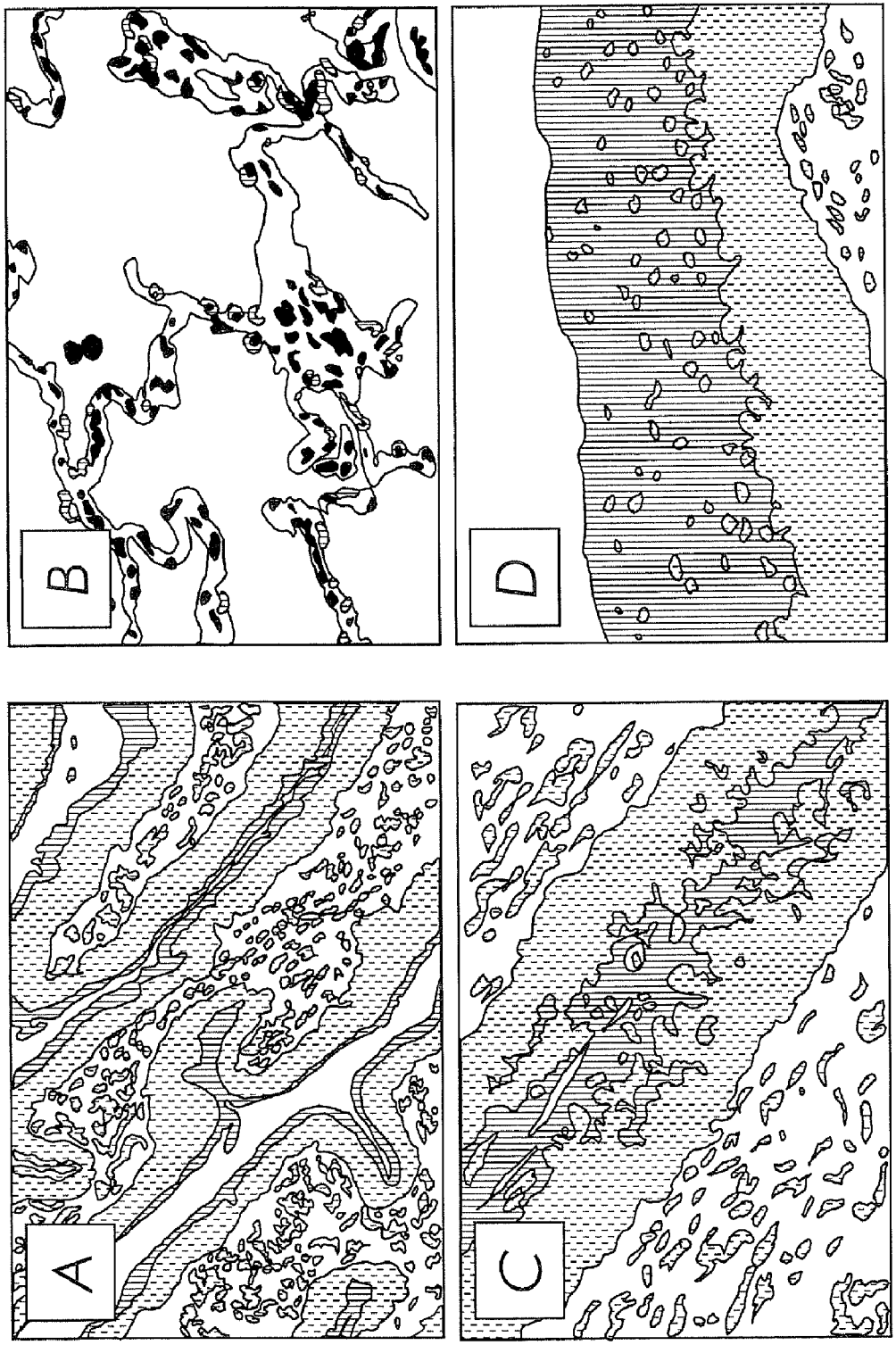
FIG. 1: DS6 immunohistochemical staining pattern on normal human tissues, A-D, with AEC (red) as the chromagen, hematoxylin counterstain: (A) Fallopian tube with apical staining of cells lining lumen, (B) apical aspect of type 2 pneumocytes of lung, (C) transitional epithelium of ureter with DS6 staining of luminal-facing aspects of inner cell layers, (D) squamous metaplasia of uterine cervix with rim pattern outlining cell membrane.

Any type of antibody may be used in the present invention. The term "antibodies" as used herein refers to all types of immunoglobulins, including IgG, IgM, IgA, IgD, and IgE. Of these, IgM and IgG are particularly preferred. The antibodies may be monoclonal or polyclonal (with monoclonal antibodies preferred) and may be of any species of origin, including (for example) mouse, rat, rabbit, horse, or human. See, e.g., M. Walker et al., *Molec. Immunol.* 26, 403-11 (1989). Antibody fragments that retain specific binding to the protein or epitope bound by DS6 are included within the scope of the term "antibody" and include, for example, Fab, F(ab')2, and Fc fragments, and the corresponding fragments obtained from antibodies other than IgG. Such fragments can be produced by known techniques. The antibodies may be chimeric or humanized, particularly when they are used for therapeutic purposes.

Subjects or patients with whom the instant invention is concerned are primarily human subjects, but the invention may also be employed with other mammalian subjects such as dogs, cats, and horses for veterinary purposes. Subjects may be male or female.

Applicants specifically intend that all United States patent references cited herein be incorporated herein by reference in their entirety.

1. Antibody Production.

Monoclonal antibodies of the present invention may be prepared using any technique that provides for the production of antibody molecules by continuous cell lines in culture. These include, but are not limited to, the hybridoma technique, the human B-cell hybridoma technique, and the EBV-hybridoma technique (Kohler, G. et al. (1975) *Nature* 256: 495-497; Kozbor, D. et al. (1985) *J. Immunol. Methods* 81:31-42; Cote, R. J. et al. (1983) *Proc. Natl. Acad. Sci.* 80:2026-2030; Cole, S. P. et al. (1984) *Mol. Cell Biol.* 62:109-120). Briefly, the procedure is as follows: an animal is immunized with antigen or immunogenic fragments or conjugates thereof. For example, haptenic oligopeptides of antigen can be conjugated to a carrier protein to be used as an immunogen. Lymphoid cells (e.g. splenic lymphocytes) are then obtained from the immunized animal and fused with immortalizing cells (e.g. myeloma or heteromyeloma) to produce hybrid cells. The hybrid cells are screened to identify those that produce the desired antibody.

Human hybridomas, which secrete human antibody, can be produced by the Kohler and Milstein technique. Although human antibodies are especially preferred for treatment of human, in general, the generation of stable human-human hybridomas for long-term production of human monoclonal antibody can be difficult. Hybridoma production in rodents, especially mouse, is a very well established procedure and thus, stable murine hybridomas provide an unlimited source of antibody of select characteristics. As an alternative to human antibodies, the mouse antibodies can be converted to chimeric murine/human antibodies by genetic engineering techniques. See V. T. Oi et al., *Bio Techniques* 4(4):214-221 (1986); L. K. Sun et al., *Hybridoma* 5 (1986).

In addition, techniques developed for the production of "chimeric antibodies", the splicing of mouse antibody genes to human antibody genes to obtain a molecule with appropriate antigen specificity and biological activity can be used (S. L. Morrison, et al. *Proc. Natl. Acad. Sci.* 81, 6851-6855 (1984); M. S. Neuberger et al., *Nature* 312:604-608 (1984); S. Takeda, S. et al., *Nature* 314:452-454 (1985)). Alternatively, techniques described for the production of single chain antibodies may be adapted, using methods known in the art, to produce CA6-specific single chain antibodies. Antibodies with related specificity, but of distinct idiotypic composition, may be generated by chain shuffling from random combinatorial immunoglobin libraries (D. R. Burton, *Proc. Natl. Acad. Sci.* 88, 11120-3 (1991)).

Antibodies may also be produced by inducing in vivo production in the lymphocyte population or by screening immunoglobulin libraries or panels of highly specific binding reagents as disclosed in the literature (R Orlandi et al., *Proc. Natl. Acad. Sci.* 86, 3833-3837 (1989)); G. Winter et al., *Nature* 349, 293-299 (1991)).

Polyclonal antibodies used to carry out the present invention may be produced by immunizing a suitable animal (e.g., rabbit, goat, etc.) with the antigen to which monoclonal antibody DS6 binds, collecting immune serum from the animal, and separating the polyclonal antibodies from the immune serum, in accordance with known procedures. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

Antibodies that bind to the same epitope (i.e., the specific binding site) that is bound by the DS6 antibody can be identified in accordance with known techniques, such as their ability to compete with labeled antibody to in binding to CA6 in a competitive binding assay.

Monoclonal antibodies specific for CA6 epitope can be used to produce anti-idiotypic (paratope-specific) antibodies. See e.g., McNamara et al., *Science* 220, 1325-26 (1984), R. C. Kennedy, et al., *Science* 232, 220 (1986). These antibodies resemble the CA6 epitope and thus can be used as an antigen to stimulate an immune response against CA6, or to screen other antibodies for the ability to specifically bind to the same epitope bound by monoclonal antibody DS6.

DS6 can also be bound to a column (such as Protein A/G) and used to obtain purified CA6 antigen from a variety of sources, including human tissues/tumors and cancer cell lines that produce CA6. Such purified CA6 antigen can then be used to produce additional antibodies (monoclonal and/or polyclonal) by methods described above. Some of these antibodies may react with the DS6 epitope while others can recognize different epitopes on CA6. In one example, enzyme immunoassay to detect antigens in human body fluids often use a combination of antibodies that recognize different, nonsterically interfering epitopes on the same antigen. For this purpose, a column containing immobilized neuraminidase could be used to desialylate purified CA6; the desialylated CA6 can then be used as an immunogen to produce antibodies (monoclonal and/or polyclonal) that react with non-DS6 epitopes on CA6. These antibodies could then be used as either capture and/or tracer antibodies in an enzyme immunoassay for quantitation of the CA6 antigen for use in monitoring of CA6 in pathologic states.

2. Immunoassay Techniques.

Those skilled in the art will be familiar with numerous specific immunoassay formats and variations thereof, which may be useful for carrying out the method disclosed herein. See generally E. Maggio, Enzyme-Immunoassay, (1980)(CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies as described herein may be coupled or conjugated to a solid support suitable for a diagnostic assay (e.g., beads, plates, slides or wells formed from materials such as latex or polystyrene) in accordance with known techniques, such as precipitation. Antibodies as described herein may likewise be conjugated to detectable groups such as radiolabels (e.g., $^{35}S$, $^{125}I$, $^{131}I$), enzyme labels (e.g., horseradish peroxidase, alkaline phosphatase), fluorescent labels (e.g., fluorescein), chemiluminescent labels (e.g., acridinium groups, metalloporphyrins such as phthalocyanine dyes, luminol, etc.), metal atoms (e.g., technetium-99m), etc., in accordance with known techniques. See, e.g., U.S. Pat. No. 4,472,509 to Gansow (metal chelates to monoclonal antibodies); U.S. Pat. No. 5,061,641 to Schochat et al.; and U.S. Pat. No. 4,861,869 to Nicoleotti et al. (radiolabelling proteins).

Immunoassays, or other types of assays to detect and/or quantitate the level of the CA6 antigen in samples as described below, may be used in screening assays to detect pathologic states associated with aberrant levels of CA6 expression (e.g., tumors, inflammatory states), diagnostic studies, prognostic studies, or to monitor the progression or diminution of CA6 expression in correlation with disease state.

Samples that may be collected for use in carrying out the immunoassay may be tissue samples from the organ or tissue of interest within the subject, such tissue generally of most interest being those types of tissues/cells that express differing amounts of CA6 in pathologic states as compared to non-pathologic states, or biological fluids such as blood (including blood fractions such as blood plasma or blood serum), urine, cerebrospinal fluid, etc). Examples may include overexpression or aberrant expression of CA6 in various types of malignancies as will be seen in the Tables below (e.g. ovarian cancer, endometrial cancer, pancreatic cancer, breast cancer, urinary bladder cancer, lung cancer, etc.), as well as overexpression or aberrant expression in other pathologic states, such as overexpression of CA6 by pneumocytes in lungs disease, for example, pneumonia.

A biological sample may be a cell sample, with an intervening culturing step being performed between the time the cell sample is collected from the subject and the immunoassay is carried out on the biological sample.

For immunohistological techniques, a tissue sample is collected from the subject, and the presence or absence of binding of an antibody of the invention is detected. The presence of binding of the antibody in an abnormal pattern or a pattern indicative of a tumor or cancer indicates the presence of a tumor or cancer in the subject from which the tissue sample is collected. The presence of the antigen in a metastatic tumor deposit can also be used to determine a likely source of the primary tumor. Any suitable immunohistology format may be used. The tissue sample may include patient biopsies, resections or cells for cytologic study. A similar technique to immunohistology is the use of similar techniques to detect and/or phenotype cells in body fluids or other suspensions as is used for flow cytometric examination.

For in vivo diagnostic purposes the antibody according to the invention is coupled to or provided with a suitable externally detectable label, such as e.g., a radiolabel as described above or a metal atom (e.g., technetium-99m), and administered to a subject (e.g., by intraveneous or intraarterial injection), in an amount sufficient to produce an externally detectable signal, whereupon the possible localized accumulation of antibody in the body is determined, with a localized accumulation of the antibody (in a region other than that which would ordinarily be expected for normal subjects or subjects free of disease) indicating the present of a tumor in that subject.

3. Therapeutic Antibodies and Methods.

Monoclonal antibodies used for therapy (i.e., in a method of combating cancer) may be monoclonal antibodies per se or monoclonal antibodies coupled to a therapeutic agent. Such antibodies are referred to herein as therapeutic monoclonal antibodies. Any therapeutic agent conventionally coupled to a monoclonal antibody may be employed, including (but not limited to) radioisotopes, cytotoxic agents, and chemotherapeutic agents (See generally *Monoclonal Antibodies and Cancer Therapy* (R. Reisfeld and S. Sell Eds. 1985)(Alan R. Liss Inc. NY); U.S. Pat. No. 5,558,852 to Bigner and Zalutsky; U.S. Pat. No. 5,624,659 to Bigner and Zalutsky).

Therapeutic agents may be conjugated or coupled to the antibody by direct means or indirect means (e.g., via a chelator), such as the Iodogen method or with N-succinimidyl-3-(tri-n-butylstanyl)benzoate (the "ATE method"), as will be apparent to those skilled in the art. See, e.g., M. Zalutsky and A. Narula, *Appl. Radiat. Isot.* 38, 1051 (1987).

Examples of radioisotopes, which may be coupled to a therapeutic monoclonal antibody, include, but are not limited to, $^{131}I$, $^{90}Y$, $^{211}At$, $^{212}Bi$, $^{67}Cu$, $^{186}Re$, $^{188}Re$, and $^{212}Pb$. Examples of chemotherapeutic agents, which may be coupled to a therapeutic monoclonal antibody, include, but are not limited to, methotrexate. Examples of cytotoxic agents, which may be coupled to a therapeutic monoclonal antibody, include, but are not limited to, ricin (or more particularly the ricin A chain).

The monoclonal antibodies of the invention can be conjugated to and used as targeting agents for genes (immunogenes, suicide genes), immunoliposomes, boron neutron capture therapy, photosensitizers for photodynamic therapy, and other types of therapies that can be directed by antibodies.

It will be appreciated that monoclonal antibodies per se which are used as therapeutic monoclonal antibodies incorporate those portions of the constant region of an antibody necessary to evoke a therapeutically useful immunological response in the subject being treated.

Therapeutic monoclonal antibodies may be provided in lyophylized form in a sterile aseptic container or may be provided in a pharmaceutical formulation in combination with a pharmaceutically acceptable carrier, such as sterile pyrogen-free water or sterile pyrogen-free physiological saline solution.

The therapeutic methods disclosed herein may be employed with subjects suspected of having a variety of tumors, whether primary or metastatic or micrometastatic (see Tables below), of particular importance are tumors of the ovary, endometrium, breast, urinary bladder, pancreas and lung. DS6 may also be of therapeutic use in other types of neoplasms, especially if used as part of a panel or combination of therapeutic antibodies, each with different specificities (Smith, N. L. et al, Human Antibodies, 9, 61-65, (1999); Oldham, R. K., Mol Biother., 3, 148-161, (1991)).

For administration, the antibody will generally be mixed, prior to administration, with a non-toxic, pharmaceutically acceptable carrier substance (e.g. normal saline or phosphate-buffered saline), and may be administered using any medically appropriate procedure, e.g., intravenous or intra-arterial administration, injection into the cerebrospinal fluid). In certain cases, intradermal, intracavity, intrathecal or direct administration to the tumor or to an artery supplying the tumor is advantageous.

Dosage of the antibody will depend, among other things, on the tumor being treated, the route of administration, the nature of the therapeutic agent employed, and the sensitivity of the tumor to the particular therapeutic agent. For example, the dosage will typically be about 1 to 10 micrograms per Kilogram subject body weight. In another example, where the therapeutic agent is 3 the dosage to the patient will typically be from 10 mCi to 100, 300 or even 500 mCi. Stated otherwise, where the therapeutic agent is $^{131}$I, the dosage to the patient will typically be from 5,000 Rads to 100,000 Rads (preferably at least 13,000 Rads, or even at least 50,000 Rads). Doses for other radionuclides are typically selected so that the tumoricidal dose will be equivalent to the foregoing range for $^{131}$I. The antibody can be administered to the subject in a series of more than one administration, and regular periodic administration will sometimes be required.

The present invention is explained in greater detail in the following non-limiting Examples. Abbreviations used: mab (monoclonal antibody), TAA (tumor-associated antigen), IH (immunohistochemistry/immunohistochemical), kiloDalton (kDa).

EXAMPLE 1

Monoclonal Antibody DS6 Detects a Tumor-Associated Sialoglycotope Expressed on Human Serous Ovarian Carcinomas We have recently developed a murine monoclonal antibody (mab), clone DS6, using human serous ovarian carcinoma as the immunogen (Smith, N. L. et al., Human Antibodies, 9, 61-65, (1999); Kearse, K. P. et al, Int. J. Cancer, in press, (2000)). We now report the immunohistochemical (IH) distribution of the DS6-detected antigen, CA6, in normal adult human tissues and selected neoplasms and characterize the epitope as a sialoglycotope.

1. Materials and Methods

Hybridoma production. Immunizations, fusions and screening were performed essentially as described previously using P3X63-Ag8.653 myeloma cells with human serous ovarian carcinoma as the immunogen (Wennerberg, A. E. et al., Am. J. Pathol., 143(4), 1050-1054 (1993)). Institutional Animal Care and Use approval was obtained. Preliminary and secondary screenings were by avidin-biotin IH (mouse IgG peroxidase kit, Vector Laboratories, Burlingame, Calif.) on tissue sections of ovarian carcinomas and selected normal adult tissues. DS6 was chosen for further studies and, after several rounds of single cell cloning by limiting dilution, was isotyped as an IgG1 (ImmunoType Kit, Sigma Chemicals, St. Louis, Mo.). Supernatant was collected in batch for the studies in this report from DS6 cells grown in DMEM-F12 supplemented with 10% horse serum. Quantitation of murine IgG1 in the supernatant was by EIA methodology (performed by the East Carolina University Hybridoma Core Facility, Greenville, N.C.).

Immunohistochemistry. Tissue culture supernatant (40 ug DS6/ml) was used for IH as above with AEC (Vector Laboratories) as the chromagen. Frozen cryostat tissue sections were air-dried, acetone-permeabilized while formalin-fixed, paraffin-embedded tissue sections were de-waxed through solvents and rehydrated, prior to blocking of endogenous peroxidase with methanol/hydrogen peroxide and subsequent immunostaining. Mouse IgG1 was used as a negative control mab. Anti-transferring receptor mab (IgG1) was used as a positive control on frozen cryostat sections while anti-smooth muscle myosin mab (IgG1) was used as a positive control on formalin-fixed tissues (all control antibodies from DAKO, Carpenteria, Calif.).

Human adult tissues. Samples of grossly normal, incidental tissues were obtained fresh from either autopsy or the surgical bench from individuals without significant pathology in the primary organ or tissue; half were used for air-dried, acetone-permeabilized cryostat sections and half were fixed in buffered formalin and paraffin-embedded. Additional normal tissues as well as a pilot selection of gynecologic and related neoplasms were obtained from the archival tissue stores of formalin-fixed, paraffin-embedded tissue blocks of the University hospital (Table 1 and Table 2). Fresh specimens of serous ovarian tumors and normal fallopian tubes were obtained from surgical cases and cryostat sections were cut for chloroform extraction studies. Use of incidental human tissues had prior approval of the Institutional Review Board.

Following completion of the normal tissue distribution and pilot study on gynecologic tumors, an expanded study was undertaken. 296 formalin-fixed, paraffin-embedded human gynecologic neoplasms were immunohistochemically examined using DS6 as the primary antibody (Table 3). A large study of non-gynecologic neoplasms followed (n=approx 1200) as seen in Tables 4-8.

Pretreated and/or preabsorbed immunohistochemical studies. For periodic oxidation of carbohydrates, formalin-fixed, paraffin-embedded sections of normal human stomach, small bowel, colon, fallopian tube, breast and serous ovarian carcinoma were pretreated, prior to IH, with 20 mM periodic acid in 0.5M acetate buffer, pH 5.0 as described by Cao (Cao, Y. et al., J. Histochem. & Cytochem. 45(11), 1547-1557 (1997); Cao, Y. et al., Tumor Biol. 19(1), 88-99 (1998).). Parallel control sections were incubated in acetate buffer without periodic acid to control for loss of reactivity due to pH or buffer. For detection of sialic acid, 0.02 U/ml neuraminidase from Vibrio cholerae (reacts with sialic acids in α2-3, -6, -8 linkages, Boehringer Mannheim/Roche, Indianapolis, Ind.), in 0.01M Ca++ in PBS was used to pretreat formalin-fixed tissue sections of the above tissues with parallel control sections pretreated with Ca++/PBS buffer without neuraminidase. An additional control for the adequacy of sialic acid removal (via unmasking of PNA lectin-binding sites) was the inclusion of a section of formalin-fixed kidney, run as above, but stained with PNA-biotin (EY Labs, San Mateo, Calif.) in place of the DS6 primary and biotin-labeled secondary antibodies. For removal of glycolipids prior to DS6 immunostaining, unfixed, air-dried cryostat sections of normal fallopian tubes and serous ovarian tumors were placed in 5% chloroform in methanol for 10 minute (Zhang, S. et al., *Int. J. Cancer*, 73, 50-56 (1997)).

To determine if DS6 reacts with several commercially available, highly purified carbohydrate antigens (sTn, Tn, Tf, sLea, Calbiochem, La Jolla, Calif.), the antigens were used to preabsorb DS6 prior to immunostaining (Taylor, C. R., In: C. R. Taylor (ed.), *Immunomicroscopy: A diagnostic tool for the surgical pathologist*, pp. 23-43, W.B. Saunders, Philadelphia (1986); Elias, J. M., *Immunohistopathology: a practical approach to diagnosis*, pp. 53-56, American Society of Clinical Pathologists, USA (1990)). Briefly, carbohydrate antigens were added to DS6 supernatant at 10 ug, 50 ug, 250 ug and 500 ug carbohydrate to 4 ug DS6 and allowed to react at 4° C. overnight. This preabsorbed supernatant was then used by IH to study sections of formalin-fixed, paraffin-embedded serous ovarian carcinomas and compared to control sections stained with unabsorbed DS6 supernatant.

Double-immunolabel, two-color IH on tissue sections. Small sections (up to 1.0 cm) of eight formalin-fixed and paraffin-embedded serous adenocarcinomas and a metastasis of each were re-embedded into two paraffin blocks for single antibody and double label/sequential IH (Battifora, H., *Lab. Invest.*, 55, 244-248 (1986)). Seven of the cases of adenocarcinoma had their primary site in the ovary, and one case was a primary papillary serous carcinoma of the peritoneum. A section of normal fallopian tube was also included in each block. A manufacturer's protocol (Vector Laboratories) for two-color, double-label IH was used: in brief, one of the murine mabs is used in a standard avidin-biotin IH technique with DAB (brown product, Vector Laboratories) as chromagen and then the entire process is repeated on the same slide using the alternate murine mab with VIP ("Very Intense Purple"; purple product, Vector Laboratories) as the chromagen. DS6 (neat) supernatant was used as one mab and a murine anti-Ca125 (OCH125 Level 1, an IgG1, Signet Laboratories, Dedham, Mass.) as the alternative mab. DAB was consistently used as the first chromagen and VIP as the second chromagen in the sequence. For double-label studies with both DS6 and OC125, the order of the primary antibodies was switched while maintaining the order of the chromagens so that each mab was evaluated both as a first and second mab in the sequence. Controls consisted of a primary mab (DS6 or OC125) with DAB followed by a mouse ascites negative control (Signet Laboratories) as the second mab with VIP. Antigen retrieval (10 mM, pH 6.0 citrate buffer) by microwave proceeded all double-label staining to assure antigen detection by mab OC125.

Immunoblotting and SDS-PAGE gel electrophoresis. Lysates of OVCAR5, a human ovarian carcinoma cell line (a generous gift from Dr. Thomas Hamilton, Fox Chase Cancer Center, Philadelphia, Pa.) that is reactive with DS6 by IH, were analyzed on one and two-dimensional SDS-polyacrylamide gel electrophoresis as previously described (Van Leeuwen, J. E. M. and Kearse, K. P., *J. Biol. Chem.*, 271, 25345-25349 (1996)). Gels were transferred to a nitrocellulose membrane and probed with DS6 or control antisera diluted in PBS containing 5% powdered milk, washed, and incubated with protein A-HRP (ICN, Irvine, Calif.) in PBS (5% milk). Protein A-HRP complexes were visualized by chemiluminescence performed according to manufacturer's instructions (Pierce Chemical Company, Rockford, Ill.). N-linked glycans were removed from precipitated proteins using an Enzymatic Deglycosylation kit (Glyko, Inc., Novato, Calif., USA).

2. Results

Distribution of CA6 in normal tissues and tumors by IH. The results of IH staining using DS6 on formalin-fixed, paraffin-embedded tissues are similar to those obtained on acetone-permeabilized cryostat sections, consistent with an epitope that is fairly resistant to the effects of formalin-fixation. The IH pattern of DS6 on cells of normal adult tissues is predominately an apical, epithelial cell membrane localization in cells lining certain tubular or saccular structures (e.g., fallopian tube, pulmonary alveoli) and along the luminal-facing aspect of the inner layers of some stratified epithelia, such as urothelium (FIG. 1, A-C). In a few instances, such as metaplastic cervical epithelium and squamous metaplasia of amnion, the entire cell membrane can be decorated giving a rim pattern to the cell (FIG. 1, D). There is absent to minimal cytoplasmic expression of the antigen in any of the normal human adult epithelia studied.

The immunohistochemical distribution of the CA6 antigen in various types of normal adult tissues in given in Table 1. In normal adult tissues, the CA6 antigen is most consistently detected in fallopian tube epithelium, urothelium and type 2 pneumocytes. In other tissues that have DS6 immunoreactivity, the CA6 antigen has a more inhomogeneous and variable expression pattern. This is particularly evident in ductal structures, where expression can vary from one duct cross section to another within a given histologic preparation.

Figure 2:
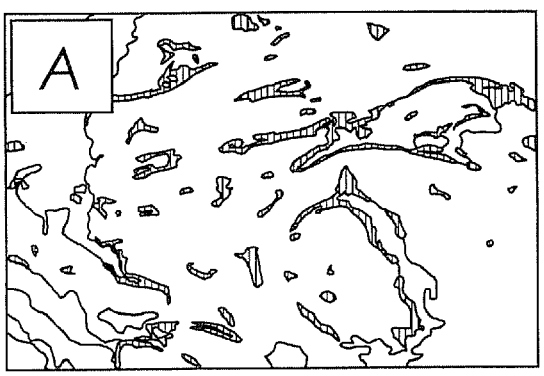
FIG. 2: (A) DS6 immunoperoxidase buffer control, i.e., without neuraminidase, on serous ovarian carcinoma, (B) DS6 immunoperoxidase on serous ovarian carcinoma following neuraminidase (*Vibrio cholerae*) treatment. C-F: Double label, sequential two color immunohistochemical staining of serous ovarian carcinomas with DS6 and OC125, hematoxylin counterstain: (C) DS6 (DAB, brown) followed by mouse Ig control (VIP, purple) shows a typical staining pattern for DS6 on tumors with both luminal and cytoplasmic staining, (D) OC125 (DAB, brown) followed by mouse Ig control (VIP, purple) shows OC125 with a luminal pattern and a focus demonstrating a rim pattern along tumor cell membranes, (E) DS6 (DAB) staining followed by OC125 (VIP) on a tumor demonstrating a discreet area of staining (purple chromagen) that is DS6-nonreactive but OC125-reactive, (F) OC125 (DAB) staining followed by DS6 (VIP) staining reveal areas of DS6-reactivity that were not detected by OC125.
Figure 2:
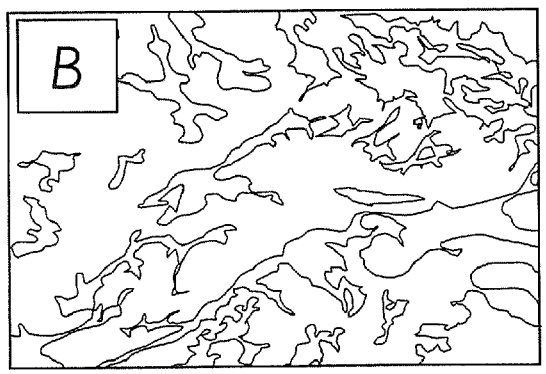
Figure 2:
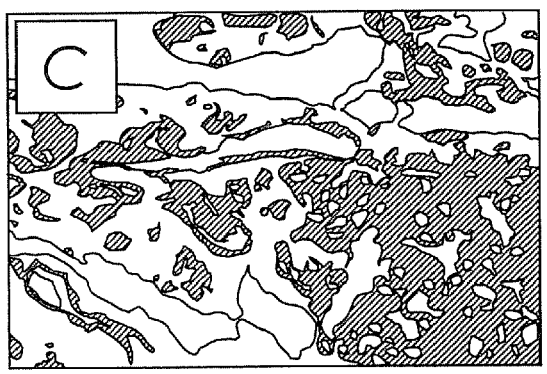
Figure 2:
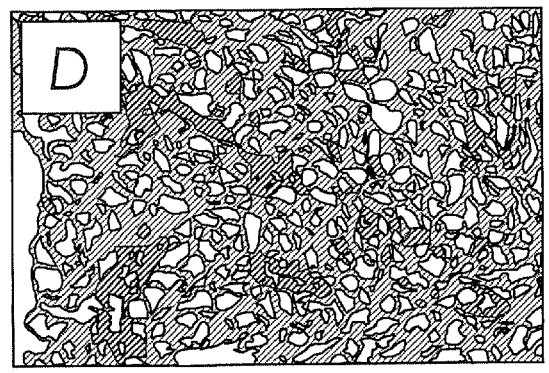
Figure 2:
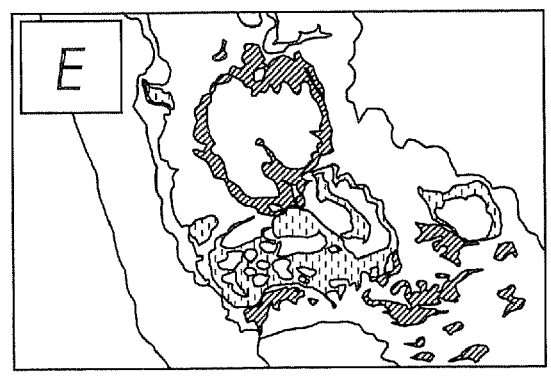
Figure 2:
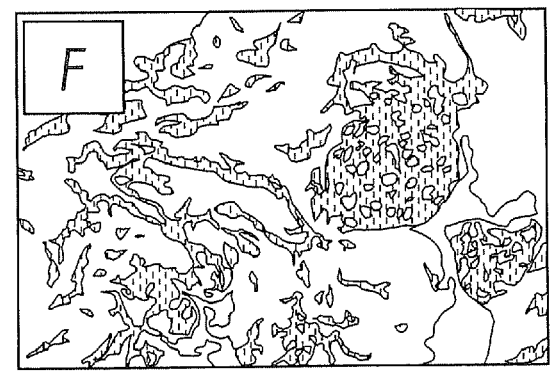

In a pilot study of selected gynecologic neoplasms (Tables 2), CA6 is expressed along the apical membranes of many cells in ovarian serous cystadenomas. In ovarian serous adenocarcinomas, the level of CA6 expression is more intense and is additionally seen in the cytoplasm of many malignant cells and extracellularly within gland lumen (FIG. 2, C). A similar luminal/apical pattern with variable cytoplasmic staining is also seen in the other adenocarcinomas that are DS6 immunoreactive. Mucinous ovarian tumors are not characteristically DS6 immunoreactive as no reactivity is seen in benign and borderline mucinous tumors and is only seen quite focally in 3 of 9 mucinous adenocarcinomas. CA6 is not detected in normal or hyperplastic mesothelium and does not appear to be characteristic of mesotheliomas (1/6), but is readily detected in serous surface carcinomas of the peritoneum (3/3).

Sensitivity of CA6 epitope to periodic acid, neuraminidase, and chloroform extraction. To characterize the CA6 epitope, sections of DS6-reactive (IH) fallopian tube and serous ovarian carcinoma, as well as DS6 nonreactive stomach, small bowel, colon and breast, were subjected to a series of pretreatments with either periodic acid or neuraminidase (*V. cholera*) prior to immuonostaining with DS6. Pretreatment of the tissue sections with either periodic acid or neuraminidase (sialidase) prior to IH with DS6 results in complete abolishment of DS6 immunoreactivity in the sections of fallopian tube and ovarian carcinoma and no DS6 immunoreactivity was unmasked in any of the sections of gastrointestinal tissues or breast. DS6 reactivity remained unaffected in the buffer control sections (FIG. 2, A-B). Preabsorption of DS6 supernatant with commercially available purified carbohydrate antigens (sTn, sLea, Tf, Tn) under conditions of antigen excess failed to reduce the intensity of DS6 immunostaining of serous ovarian carcinomas (data not shown).

Chloroform extraction studies were performed on sections of fallopian tubes (2) and serous ovarian tumors (3) prior to immunostaining with DS6. Control cryostat sections of fallopian tubes and ovarian tumors show strong staining with DS6 in the formalin-fixed as well as in the acetone-permeabilized slides. The chloroform-pretreated slides, stained with DS6, reveal mild to moderate reduction in staining intensity in fallopian tubes and ovarian tumors respectively.

Figure 3:
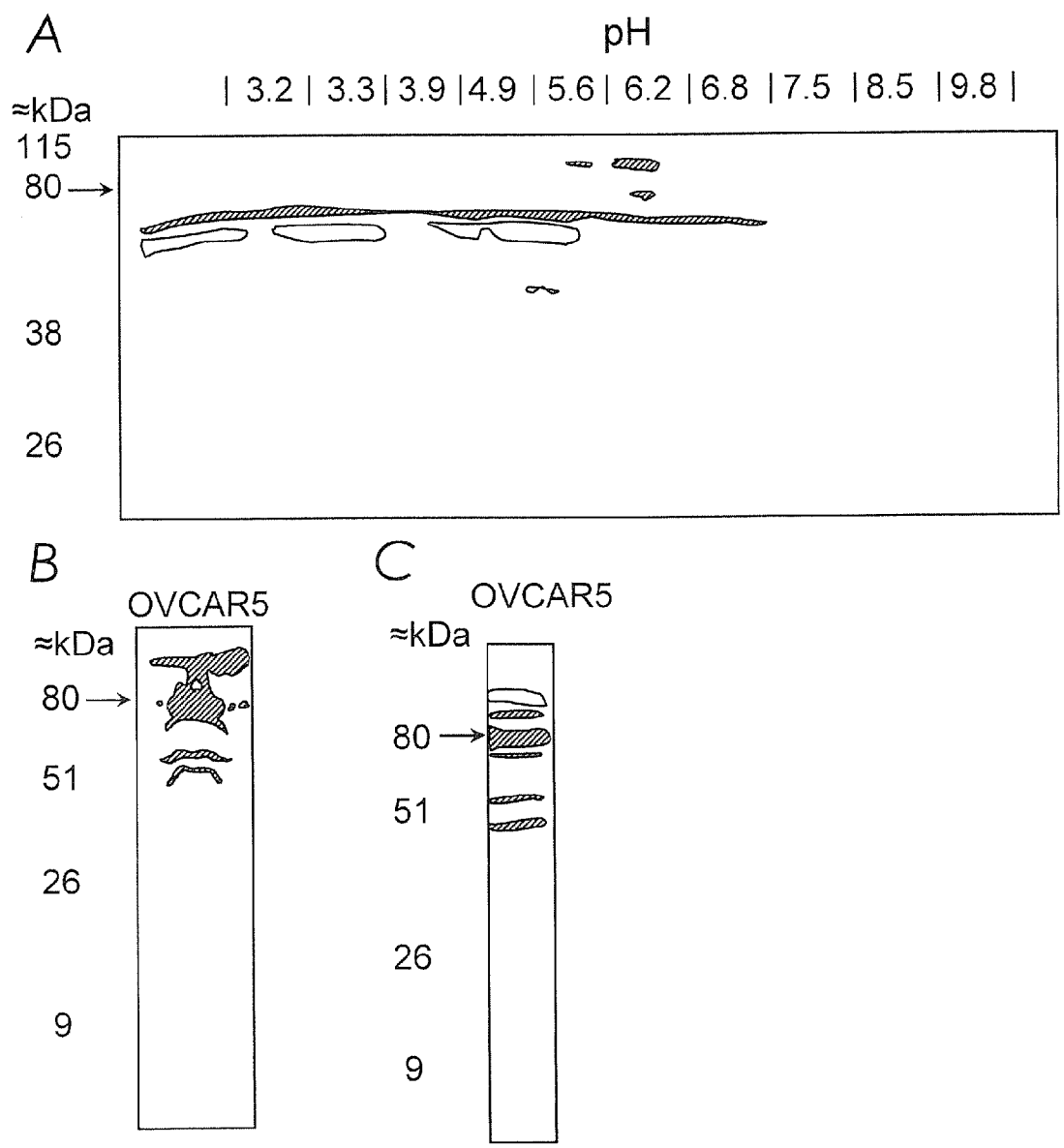
FIG. 3: (A) Two-dimensional nonequillibrium pH gradient gel electrophoresis (NEPHGE) analysis of the DS6-detected CA6 antigen. Samples were analyzed on NEPHGE gels (pI range ~3.2-7.8) in the first dimension, followed by 13% SDS-PAGE gels in the second dimension, all under reducing conditions. (B) One dimensional SDS-PAGE analysis on 13% gels under reducing conditions and in (C) on 10% gels under nonreducing conditions.

Immunoblotting and SDS-polyactylamide gel electrophoresis. OVCAR5, a human ovarian carcinoma cell line reactive with DS6 by IH (data not shown) was used as a reproducible source of antigen. Anti-DS6 immunoblots of OVCAR5 lysates gave a predominant band at approximately 80 kilodaltons (kDa), with minor species at 75 kDa, 52 kDa, and 48 kDa (FIG. 3, B). Migration is similar under both reducing and nonreducing conditions and no reactivity with control (isotype matched) antibody is observed (FIG. 3, B-C). Analysis on two-dimensional nonequilibrium pH gradient electrophoresis (NEPHGE) gels indicates an isoelectric point of approximately 6.2-6.5 (FIG. 3, A). Digestion studies with PNGase F result in a reduction in molecular weight of the 80 kDa species to approximately 75 kDa, consistent with the presence of one to two N-liked glycan chains (data not shown).

Double-immunolabel, two-color IH of tissue sections. Single antibody and double-label, two-color IH studies were performed using mabs DS6 and OC125 to determine if CA6 and CA125 are expressed by the same or differing tumor cell populations. Both antibodies reacted with the luminal aspect of fallopian tubes but only OC125 reacted with the mesothelium of the fallopian tubes. All eight primary papillary serous adenocarcinomas and their metastases show moderate to strong positivity for DS6 and OC125 with the exception of one primary tumor that has only scattered focal positive cells with either mab. Comparison of tumors stained individually with either DS6 or OC125 reveal that they react with roughly similar proportions of tumor cells although the intensity of staining is more pronounced with DS6. While both the CA6 and CA125 antigens are expressed along the luminal membranes of the neoplastic cells in many areas and in most tumors strikingly similar IH patterns can be found, there are some distinct differences. CA6 often has an additional prominent cytoplasmic component while CA125 will occasionally show a distinct pattern of circumferential membrane expression on the neoplastic cells in several of the tumors, giving a honeycomb appearance to the tumor that is not as characteristic of CA6 (FIG. 2, C-D). When both DS6 and OC125 are used in sequential, two-color IH, intensely positive dark chromagen results from overlapping, dual localization of chromagens in many areas of the tumors. This dark chromagen can be difficult to distinguish from an intensely positive deposition from the first mab/chromagen (brown, DAB) reaction alone. However, in most tumors, focal areas of chromagen deposition resulting from the second mab/chromagen (purple, VIP) reaction can be clearly visualized (FIG. 2, E-F). Such areas result from the second mab in the sequence reacting with an antigen that is not detected by the prior application of the first mab.

Following the immunohistochemical studies above, a greatly expanded number of gynecologic neoplasms, as well as non-gynecologic neoplasms, were similarly studies for DS6 immunoreactivity. The results are listed in Tables 3-8. As can be seen, the CA6 antigen is not restricted to ovarian carcinomas but can be expressed by a variety of other carcinomas, including, but not limited to, those of the breast, endometrium, pancreas, urinary bladder and lung.

3. Discussion

As CA6 has only a limited distribution in the normal tissues studied, is not detected in normal ovarian surface epithelium, yet is expressed in serous ovarian carcinomas which arise from the surface epithelium (18/18), it can be described as a TAA (Suresh, M. R., *Anticancer Res.*, 16(4B), 2273-2277 (1996); Khawli, L. A. and Epstein, A. L., *Q.J. Nucl. Med.*, 41, 25-35 (1997)). Immunohistochemical studies of DS6 on a wide variety of human carcinomas, lymphomas and sarcomas can be seen in Tables 2-8 and demonstrate that DS6 is not a pan-carcinoma marker but rather is characteristic of specific types of epithelial malignancies (e.g., characteristic of serous ovarian carcinomas but seldom reactive with colon carcinomas). Analyzing the IH distribution of CA6 in normal tissues, similarities, as well as differences, can be noted to other reported TAAs. For instance, the pattern of reactivity in the anterior pituitary has also been described for CA19-9 and EMA (Okubo, T. and Okabe, H., *Acta Neuropathol.*, 93, 471-476 (1997); Pernicone, P. J. et al., In: S. S. Sternberg (ed.), *Histology for pathologists, second edition*, pp 1053-1074, Lippincott-Raven, Philadelphia (1997)), the staining of the intracellular canaliculus of parietal cells is a feature of the MUC1-related mab HMFG2 (Walker, M. M. et al., *J. Clin. Pathol.*, 48, 832-834 (1995)), while luminal staining of ductal structures is variably reported for a large number of TAAs, including the MUC1 mucin family and histo-blood group related antigens (Arklie, J. et al., *Int. J Cancer*, 28, 23-29 (1981); Zhang et al., supra (1997); Cao, Y. et al., *Histochem. Cell Biol.*, 106, 197-207 (1996)). Reports of mabs to TAAs have been numerous and, as TAAs are not unique to tumors, it is not unexpected that some similarities in their IH distribution in normal epithelial tissues would be seen. The reported distribution of epithelial TAAs can also vary in the hands of different investigators, perhaps reflecting differences in methodologies, grading systems, antibody preparation, tissue preparation, or fixation (Zhang et al., supra (1997); Stein, R. et al., *Int. J Cancer*, 47, 163-169 (1991); Buist, M. R. et al., *J. Clin. Pathol.*, 48, 631-636 (1995)). We have characterized the IH distribution of DS6 in both cryostat and formalin-fixed, paraffin-embedded tissues to provide a range of experimental conditions that are in common use. Additionally, we have classified the types of DS6-reactive epithelial tissues as to the types of tissues most consistently positive versus those tissues in which the expression appears more variable. As will be discussed below, the consistent presence or absence of CA6 in certain epithelial tissues does appear to distinguish CA6 from certain other known TAAs. To further characterize CA6, additional features of the antigen were investigated.

Pretreatment of tissue sections with either periodic acid or neuraminidase from *Vibrio cholerae* gives similar results. These techniques are used to determine if the epitope is carbohydrate-based or sialic acid-dependent, respectively, and have also been used to unmask hidden epitopes such as masking of the binding sites of several MUC1 mabs by glycosylation (Cao et al., supra (1997); Cao et al, supra (1998)). The abolishment of DS6 immunoreactivity by both treatments is consistent with a carbohydrate epitope that is sialic acid-dependent. No DS6-reactive epitopes are unmasked in any of the sections by such removal of periodic-sensitive carbohydrates or sialic acid.

To determine if the CA6 sialoglycotope is expressed as a sialoglycoprotein and/or a sialoglycolipid (ganglioside), additional studies were performed. SDS-PAGE immunoblots reveal that the DS6 mab detects a predominant 80 kDa glycoprotein with N-linkages. Minor side bands are noted that may represent proteolytic degradations of the major band or are side reactivites of the antibody (i.e., carbohydrate epitope shared on more than one protein). No change in migration of the major 80 kDa band is noted between reduced and non-reduced conditions signifying a lack of interchain disulfide bonds (FIG. 3, B-C). Chloroform extraction studies are used to extract lipids from tissue sections prior to DS6 immunostaining and are then compared to DS6 immunostaining on tissue sections without prior chloroform extraction. While some general reduction in staining intensity was noted in sections of fallopian tube, a more marked reduction was noted in the sections of ovarian tumors. Whether this apparent difference in efficiency of extraction in a normal tissue (i.e., fallopian tube) as compared to tumors is quantitative or qualitative is uncertain, however, ongoing studies into the chemical nature of the epitope may help explain the significance of this finding. The sialoglycotope nature of CA6 is similar to many of the histo-blood group-related antigens such as sTn, sLea, sLex, some of which are dually-expressed as glycoproteins and glycolipids, however, unlike CA6, as glycoproteins, these are usually high molecular weight, carbohydrate rich O-linked glycoproteins (mucins) (Magnani, J. L. et al., Cancer Res., 43, 5489-5492 (1983); Muraro, R. et al., Cancer Res., 48, 4588-4596 (1988)). The immunohistochemical distribution of the histo-blood group related antigens, as reviewed by Zhang et al., would also distinguish CA6 from the above sialyated histo-blood group antigens (Zhang et al., supra (1997)). The apical-staining pattern of DS6 on type 2 pneumocytes, which lack sTn, sLea and sLex expression (Hachiya, T. et al., Virchows Arch., 434, 63-69 (1999); Atkinson, B. F. et al., Cancer Res., 42, 4820-4823 (1982)), is strikingly similar to that reported for the sTf (sialyl-Thomsen-Fridenreich) antigen (Hachiya et al., supra (1999)). However, if DS6 is reacting with the sTf epitope per se, it would be expected to demonstrate a much broader range of immunoreactivity in human tissues than is seen in our studies, including expression in DS6-nonreactive epithelia, brain, lymphoid and other mesenchymal tissues (Cao et al., supra (1996)). The DS6 preabsorption studies using commercially available, highly purified sTn, sLea, Tn and Tf carbohydrate antigens, in which the antigens failed to inhibit the tissue binding of DS6, also support CA6 being distinct from these carbohydrate antigens. Other TAAs to consider are those of approximately 80 kDa such as OC133 (Berkowitz, R. et al., Am. J. Obstet. Gynecol., 146(6), 607-612 (1983); Masuho, Y. et al., Cancer Res., 44, 2813-2819 (1984)), Ki-OCI-6-2 (Mettler, D. L. et al., Cancer, 65, 1525-1532 (1990)), and the lactoferrin-related MAM5 (Zotter, S. et al., Virchows Arch. A. Pathol. Anat. Histopathol., 406(2), 237-251 (1985)), none of which are expressed by fallopian tube, and 22-1-1, a mab to a neuraminidase resistant epitope on a 78 kDa protein, which is more characteristic of mucinous rather than serous ovarian tumors (Sonoda, K. et al., Cancer, 77(8), 1501-1509 (1996)).

Although the molecular weights of CA6 (80 kDa) and CA125 (>200 kDa) and their distribution in normal tissues differ (CA125 has been detected by IH in some normal epithelia of pancreas, ovary, fallopian tube, colon, gallbladder, stomach, endometrium, bronchus, lung, kidney and in mesothelium and amnion), the IH pattern of CA6 in our series of ovarian tumors is similar to that reported for CA125 (Davis, H. M. et al., Cancer Res., 46, 6143-6148, 1986; Nouwen, E. J. et al., Cancer Res., 46(2), 866-876 (1986); Dietel, M. et al., J. Cancer Res. Clin. Oncol., 111, 257-256 (1986); Itahashi, K. et al., Arch. Gyn. Obst., 243(3), 145-155 (1988)). Both antigens are more characteristic of ovarian serous carcinomas than ovarian mucinous neoplasms and both have a variegated distribution pattern, often with luminal accentuation (Mattes, M. et al., Cancer Res. (suppl.), 50, 880-884 (1990)). In IH studies, both antigens show a spectrum of expression ranging from strong and diffuse in some tumors to patchy and variegated patterns in other neoplasms, with strongly positive groups of cells adjacent to nonreactive foci. The double-label, two-color, sequential IH studies comparing CA6 to CA125 demonstrate that mabs DS6 and OC125, while showing extensive overlap, also show areas in which only one of the antibodies is expressed, providing additional, complementary coverage of the tumor. Such complementarity of TAA expression can have important clinical implications, whether for tailoring mab-based cancer therapies as "cocktails" matched to a given tumor's antigenic phenotype (Liao, S.-K. et al., Cancer Immunol. Immunother., 28, 77-86 (1989); Oldham, R. K., Mol Biother., 3, 148-161 (1991)), or for devising panels of tumor markers to monitor tumor progression (Cane, P. et al., Gynecologic Oncol., 57, 240-245 (1995)).

In the sections of fallopian tubes, CA125 is distributed along luminal epithelial surfaces and is readily detected in the mesothelium. Conversely, CA6, which is more intensely expressed along the fallopian tube lumen, is not detected in the mesothelium. DS6 clearly recognizes an antigen that has a similar, but not identical, distribution to the CA125 antigen, with some distinct differences in patterns and sites of antigen expression. The lack of CA6 expression in normal mesothelium could make DS6 a candidate for intraperitoneal antibody-targeted therapeutic applications.

TABLE 1

Immunohistochemical detection of CA6 in tissue sections of normal adult tissues. Acetone-permeabilized and formalin-fixed, paraffin-embedded tissues were stained with mab DS6 as the primary antibody by avidin-biotin immunohistochemistry.

| Tissue | Cryostat #positive/ #tested | Formalin-paraffin #positive/ #tested | Positive cell types/Comments |
|---|---|---|---|
| Tissues with prominent, consistent CA6 expression within and between specimens: | | | |
| Fallopian tube | 3/3 | 6/6 (8/8)[a] | Luminal/apical epithelial cell membrane |
| Lung | 2/2 | 5/5 | Apical-aspect of type II pneumocyte; occasional epithelial cell of bronchiole |
| Urothelium | 3/3 | 8/8 | Inner layers, luminal-facing aspect |
| Tissues with low-level CA6 expression, quite variable/focal within and between specimens: | | | |
| Pancreas | 2/2 | 5/6 | Luminal-aspect of small to medium ducts |
| Liver | 1/2 | 3/5 | Luminal-aspect of occasional portal bile ducts |
| Major salivary gland | nt[b] | 2/3 | Luminal-aspect of occasional medium-sized ducts |
| Kidney | 3/3 | 5/5 | Luminal-aspect of scattered cells of distal nephron |
| Endometrium, secretory | 3/3 | 3/4 | Focal luminal staining. Rare surface epithelial cell, 2/4 |
| Cervix | 2/2 | 5/6 | Focal, membrane rim pattern in metaplastic epithelium, transformation zone and 1/1 ectocervical epithelium |
| Endocervical glands | 0/2[c] | 3/6 | Focal luminal staining of some glands in transformation zone |
| Pituitary | 2/2 | 2/2 | Focal staining of rim of follicles, anterior lobe |

TABLE 1-continued

Immunohistochemical detection of CA6 in tissue sections of normal adult tissues. Acetone-permeabilized and formalin-fixed, paraffin-embedded tissues were stained with mab DS6 as the primary antibody by avidin-biotin immunohistochemistry.

| Tissue | Cryostat #positive/ #tested | Formalin-paraffin #positive/ #tested | Positive cell types/Comments |
|---|---|---|---|
| Tissues lacking CA6 expression or rare focus only: | | | |
| Cerebral cortex | 0/3 | 0/3 | |
| Cerebellum | 0/3 | 0/3 | |
| Spinal cord | 0/3 | 0/3 | |
| Large peripheral nerve | 0/3 | 0/3 | |
| Trachea | nt | 0/2 | |
| Parathyroid | 0/2 | 1/4 | One small focus of CA6 in histologically normal area of gland that elsewhere had pseudofollicle formation |
| Thyroid | 2/2 | 2/3 | Rare apical-aspect of follicular epithelial cell |
| Breast | 1/3 | 2/4 | Rare apical-aspect of epithelial cell |
| Adrenal | 0/4[d] | 0/7 | |
| Esophagus | 1/2 | 0/3 | Single focus of suprabasal cell membrane staining, membrane rim pattern |
| Stomach | 0/4[c] | 0/6 | [Intracellular canaliculas of parietal cells positive, 3/4][e] |
| Small intestine | 0/4[c] | 0/7 | |
| Large intestine | 0/4[c] | 0/6 | |
| Gallbladder | nt | 0/3 | |
| Testes | 0/4 | 0/5 | [Weak positive rete testes, collecting ductules, 2/3; epididymis negative, 3] |
| Prostate | 0/1 | 0/4 | [2 specimens included periurethral prostatic ducts, weak positive] |
| Ovary | 0/3 | 0/5 | [one inclusion cyst positive, numerous inclusion cysts negative] |
| Endometrium, proliferative | 0/2 | 0/7 | |
| Heart | 0/1 | 0/2 | |
| Skeletal muscle | 0/2 | 0/3 | |
| Thymus | nt | 0/3 | |
| Spleen | 0/2 | 0/3 | |
| Lymph node | 0/2 | 0/3 | |
| Epidermis | 0/2 | 0/5 | |
| Other non-epithelial | see comments | | Tissues consistently negative in numerous sections: mesothelium, rbc, wbc, lymphoreticular cells, fat, smooth muscle, nerve, endothelium |
| Placenta | nt | 0/5 | [Focal squamous metaplastic amnion cell, rim pattern, 3/3] Chorion nt |

Footnotes:
[a]( ) total number inclusive of double label studies;
[b]not tested;
[c]staining of wispy extracellular material;
[d]unidentified spindle cells in capsule focally positive;
[e][ ] additional specificity not counted in table.

TABLE 2

Immunohistochemical detection of CA6 in gynecologic and related neoplasms/hyperplasias. Formalin-fixed, paraffin-embedded tissue sections were stained with mab DS6 as the primary antibody by avidin-biotin immunohistochemistry.

| Tissue | #positive/ #tested |
|---|---|
| Ovarian: | |
| Serous cystadenoma | 3/3 |
| Serous borderline tumor | 5/5 |
| Serous adenocarcinoma | 11/11 (18/18)[a] |
| Mucinous cystadenoma | 0/2 |
| Mucinous borderline tumor | 0/2 |
| Mucinous adenocarcinoma | 3/9 |
| Endometroid, borderline | 0/1 |
| Endometrial: | |
| Clear cell adenocarcinoma | 2/2 |
| Papillary serous adenocarcinoma | 3/3 |
| Endometroid adenocarcinoma | 1/1 |
| Benign polyp | 0/1 |
| Peritoneum: | |
| Mesothelioma | 1/6 |
| Reactive mesothelial hyperplasia | 0/1 |
| Serous surface carcinoma of peritoneum | 2/2 (3/3) |

Footnotes:
[a]( ) total number inclusive of double label studies

TABLE 3

Expression of Tumor-Associated Antigen CA6 in Gynecological Neoplasms as Immunohistochemically Detected by Monoclonal Antibody DS6

| Neoplasm | Reactive Cases/ Total Number of Cases | Nonreactive (Cases with <1% neoplastic cells reactive) | 1+ (Cases with 1-9% neoplastic cells reactive) | 2+ (Cases with 10-49% neoplastic cells reactive) | 3+ (Cases with >50% neoplastic cells reactive) | Major Patterns of Reactivity[1] |
|---|---|---|---|---|---|---|
| *Uterine Cervix* | | | | | | |
| Squamous Cell Carcinoma | 10/14 | 4 | 4 | 3 | 3 | Me, Cy |
| Squamous Dysplasia | 0/7 | 7 | | | | |
| Endocervical Adenocarcinoma in Situ | 0/2 | 2 | | | | |
| Endocervical Adenocarcinoma | 2/3 | 1 | 1 | 1 | | Lu, Me |
| Adenosquamous Carcinoma | 2/2 | | | 2 | | Me, Cy |
| *Endometrium* | | | | | | |
| Papillary Serous Adenocarcinoma | 6/6 | | 2 | 2 | 2 | Lu, Me |
| Endometriod Adenocarcinoma | 14/16 | 2 | 7 | 4 | 3 | Lu, Me |
| Clear Cell Carcinoma | 8/10 | 2 | | 1 | 7 | Lu, Me, Cy |
| Mucinous Adenocarcinoma | 3/5 | 2 | | 1 | 2 | Me, Cy |
| Malignant Mixed Mullerian Tumor, carcinomatous component | 10/18 | 8 | 5 | 1 | 4 | Me, Cy |
| Choriocarcinoma | 0/1 | 1 | | | | |
| Molar Pregnancy | 0/3 | 3 | | | | |
| *Uterus* | | | | | | |
| Low Grade Endometrial Stroma Sarcoma | 0/3 | 3 | | | | |
| Undifferentiated Endometrial Sarcoma | 0/1 | 1 | | | | |
| Leiomyoma | 0/7 | 7 | | | | |
| Leimyosarcoma | 0/6 | 6 | | | | |
| *Ovary* | | | | | | |
| Serous Cystadenoma | 9/12 | 3 | 1 | | 8 | Lu |
| Papillary Serous Borderline Tumor | 10/10 | | 1 | 2 | 7 | Lu |
| Papillary Serous Adenocarcinoma | 56/58 | 2 | 4 | 9 | 43 | Lu, Me, Cy |
| Papillary Serous Carcinoma Metastases | 14/14 | | | 1 | 13 | Lu, Me, Cy |
| Mucinous Cystadenoma | 0/10 | 10 | | | | |
| Mucinous Borderline Tumor, Intestinal | 0/8 | 8 | | | | |
| Mucinous Borderline Tumor, Mullerian | 2/2 | | 1 | | 1 | Lu |
| Mucinous Adenocarcinoma | 0/10 | 10 | | | | |
| Clear Cell Carcinoma | 1/8 | 7 | 1 | | | Me |
| Endometriod Adenocarcinoma | 5/8 | 3 | 3 | 1 | 1 | Lu, Me |
| Benign Brenner Tumor | 6/9 | 3 | 2 | 1 | 3 | Me, Lu, Cy |
| Borderline Brenner Tumor | 1/1 | | | | 1 | Me, Cy |
| Granulosa Cell Tumor | 0/15 | 15 | | | | |
| Fibroma/Thecoma | 0/11 | 11 | | | | |
| Sertoli Cell Tumor | 0/1 | 1 | | | | |
| Yolk Sac Tumor | 0/2 | 2 | | | | |
| Struma Ovarii | 0/1 | 1 | | | | |
| Dysgerminoma | 0/3 | 2 | | | | |
| *Vulva* | | | | | | |
| Squamous Cell Carcinoma | 2/3 | 1 | 2 | | | Me, Cy |
| Hidradenoma Papilliferum | 2/2 | | 2 | | | Me |
| *Peritoneum* | | | | | | |
| Papillary Serous Surface Carcinoma | 2/2 | | | 1 | 1 | Lu, Me |
| Malignant Mesothelioma of peritoneum | 0/2 | 2 | | | | |

TABLE 3-continued

Expression of Tumor-Associated Antigen CA6 in Gynecological Neoplasms as Immunohistochemically Detected by Monoclonal Antibody DS6

| Neoplasm | Reactive Cases/ Total Number of Cases | Nonreactive (Cases with <1% neoplastic cells reactive) | 1+ (Cases with 1-9% neoplastic cells reactive) | 2+ (Cases with 10-49% neoplastic cells reactive) | 3+ (Cases with >50% neoplastic cells reactive) | Major Patterns of Reactivity[1] |
|---|---|---|---|---|---|---|
| Endosalpingiosis (nonneoplastic) | 1/1 | | 1 | | | Lu |
| Mesothelium (incidental nonneoplastic) | 0/7 | 7 | | | | |

[1]Abbreviations for Patterns of Immunohistochemical Reactivity: Lu = Luminal cell membrane, Me = Cell membrane, Cy = Cytoplasm.

TABLE 4

Expression of Tumor-Associated Antigen CA6 in Epithelial Neoplasms as Immunohistochemically Detected by Monoclonal Antibody DS6

| Neoplasm | Reactive Cases/ Total Number of Cases | Nonreactive (Cases with <1% cells reactive) | 1+ (Cases with 1-9% cells reactive) | 2+ (Cases with 10-49% cells reactive) | 3+ (Cases with >50% cells reactive) | Major Patterns of CA6 Expression |
|---|---|---|---|---|---|---|
| Breast | | | | | | |
| Infiltrating Ductal Carcinoma | 24/29 | 5 | 3 | 8 | 13 | Lu, Me, ICL |
| Infiltrating Lobular Carcinoma | 5/11 | 6 | 1 | 1 | 3 | ICL |
| Pleomorphic Lobular Carcinoma | 1/2 | 1 | | | 1 | ICL, Lu |
| Colloid Carcinoma | 6/7 | 1 | 3 | | 3 | Lu, Me |
| Invasive Apocrine Carcinoma | 1/1 | | | | 1 | ICL |
| Medullary Carcinoma | 1/1 | | | | 1 | Lu, Me, ICL |
| Tubular Carcinoma | 1/1 | | | 1 | | Lu, ICL |
| Invasive Papillary Carcinoma | 1/1 | | 1 | | | Lu, Me |
| Brain | | | | | | |
| Meningioma | 3/25 | 22 | 2 | | 1 | Cy, Me |
| Craniopharyngioma | 1/2 | 1 | 1 | | | Lu |
| Gallbladder | | | | | | |
| Gallbladder Adenocarcinoma | 3/7 | 4 | 1 | | 2 | Lu, Me |
| Cystic Duct Adenocarcinoma | 1/2 | 1 | 1 | | | Lu |
| Gastrointestinal | | | | | | |
| Colonic Adenocarcinoma | 3/21 | 18 | 2 | 1 | | Lu, Me |
| Metastatic Colon Adenocarcinoma | 0/3 | 3 | | | | |
| Mucinous Colon Adenocarcinoma | 0/6 | 6 | | | | |
| Colonic Tubular Adenoma | 0/1 | 1 | | | | |
| Cloacogenic Carcinoma | 1/3 | 2 | 1 | | | Lu, Me |
| Duodenal Adenocarcinoma | 0/1 | 1 | | | | |
| Esophageal Adenocarcinoma | 1/4 | 3 | 1 | | | Lu |
| Esophageal Squamous Carcinoma | 2/9 | 7 | | 1 | 1 | Me, Cy |
| Gastric Adenocarcinoma | 7/19 | 12 | 2 | | 5 | Lu, Me |
| Gastric Squamous Carcinoma | 1/1 | | | 1 | | Me, Cy |
| Kidney | | | | | | |
| Clear Cell Carcinoma | 13/18 | 5 | 13 | | | Me, Lu |
| Papillary Carcinoma | 3/5 | 2 | 1 | 1 | 1 | Lu, Me |
| Granular Carcinoma | 5/8 | 3 | | 2 | 3 | Me |
| Chromophobe Carcinoma | 3/4 | 1 | 2 | | 1 | Lu, Me, Cy |
| Oncocytoma | 2/2 | | | 1 | 1 | Lu, Me, Cy |
| Cortical Adenoma | 1/1 | | 1 | | | Lu, Me |
| Wilms Tumor | 1/9 | 8 | 1 | | | Lu in tubules |

TABLE 4-continued

Expression of Tumor-Associated Antigen CA6 in Epithelial Neoplasms as Immunohistochemically Detected by Monoclonal Antibody DS6

| Neoplasm | Reactive Cases/ Total Number of Cases | Nonreactive (Cases with <1% cells reactive) | 1+ (Cases with 1-9% cells reactive) | 2+ (Cases with 10-49% cells reactive) | 3+ (Cases with >50% cells reactive) | Major Patterns of CA6 Expression |
|---|---|---|---|---|---|---|
| Larynx | | | | | | |
| Squamous Cell Carcinoma | 10/27 | 17 | 8 | 1 | 1 | Me, Cy |
| Squamous Papilloma | 1/1 | | | 1 | | Lu, Me |
| Liver | | | | | | |
| Hepatocellular Carcinoma | 1/8 | 7 | 1 | | | Lu, Me, Cy |
| Lung | | | | | | |
| Adenocarcinoma | 8/12 | 4 | 4 | 1 | 3 | Lu, Me |
| Squamous Cell Carcinoma | 6/15 | 9 | 1 | 4 | 1 | Me, Cy |
| Adenosquamous Carcinoma | 1/1 | | | | 1 | Me |
| Pancreas | | | | | | |
| Adenocarcinoma | 8/9 | 1 | | 2 | 3 | 3 | Lu, Me |
| Pleura | | | | | | |
| Malignant Mesothelioma | 0/6 | 6 | | | | Me |
| Prostate | | | | | | |
| Acinar Adenocarcinoma | 4/13 | 9 | 3 | 1 | | Lu, Me |
| Prostatic Duct Adenocarcinoma | 0/5 | 5 | | | | |
| Salivary Gland | | | | | | |
| Epithelial Neoplasms [See Fig.] | 21/90 | 69 | 12 | 6 | 3 | |
| Skin | | | | | | |
| Epithelial Neoplasms [See Fig.] | 19/79 | 60 | 15 | 4 | | |
| Testicle | | | | | | |
| Teratoma, epithelial elements | 2/5 | 3 | 2 | | | Lu |
| Thyroid | | | | | | |
| Follicular Adenoma | 0/2 | 2 | | | | |
| Follicular Carcinoma | 1/17 | 16 | 1 | | | Lu |
| Hurthle Cell Adenoma | 2/5 | 3 | 1 | 1 | | Lu |
| Hurthle Cell Carcinoma | 2/5 | 3 | 1 | 1 | | Lu |
| Hyperplastic Hurthle Cell Nodule | 1/1 | | 1 | | | Lu |
| Insular Carcinoma | 1/1 | | 1 | | | Lu, Me |
| Papillary Carcinoma | 16/27 | 11 | | 9 | 7 | Lu, Me |
| Thymus | | | | | | |
| Thymoma | 0/17 | 17 | | | | Lu, Me |
| Thymic Carcinoma | 0/1 | 1 | | | | |
| Squamous Cell Carcinoma | 1/1 | | | 1 | | Lu, Me |
| Urinary Bladder | | | | | | |
| Transistional Cell Carcinoma | 18/21 | 3 | 8 | 5 | 5 | Lu, Me |
| Squamous Cell Carcinoma | 0/1 | 1 | | | | |

Abbreviations: Lu—Luminal portion of cell membrane; Me—Cell membrane; Cy—Cytoplasm; ICL—Intracytoplasmic lumina.

TABLE 5

Expression of Tumor-Associated Antigen CA6 in Skin Neoplasms as Immunohistochemically Detected by Monoclonal Antibody DS6

| Neoplasm | Reactive Cases/ Total Number of Cases | Nonreactive (Cases with <1% cells reactive) | 1+ (Cases with 1-9% cells reactive) | 2+ (Cases with 10-49% cells reactive) | 3+ (Cases with >50% cells reactive) | Major Patterns of CA6 Expression |
|---|---|---|---|---|---|---|
| Basal Cell Carcinoma | 0/19 | 19 | | | | |
| Chondroid Syringoma | 0/1 | 1 | | | | |

TABLE 5-continued

Expression of Tumor-Associated Antigen CA6 in Skin Neoplasms as Immunohistochemically Detected by Monoclonal Antibody DS6

| Neoplasm | Reactive Cases/ Total Number of Cases | Nonreactive (Cases with <1% cells reactive) | 1+ (Cases with 1-9% cells reactive) | 2+ (Cases with 10-49% cells reactive) | 3+ (Cases with >50% cells reactive) | Major Patterns of CA6 Expression |
|---|---|---|---|---|---|---|
| Cylindroma | 0/3 | 3 | | | | |
| Dermatofibroma | 0/9 | 9 | | | | |
| Dermatofibosarcoma Protuberans | 0/3 | 3 | | | | |
| Eccrine Acrospiroma | 11/13 | 2 | 10 | 1 | | Me, Lu |
| Eccrine Spiradenoma | 1/7 | 6 | 1 | | | Lu |
| Eccrine Carcinoma | 0/1 | 1 | | | | |
| Hemangioma | 0/8 | 8 | | | | |
| Leiomyoma | 0/8 | 8 | | | | |
| Leiomyosarcoma | 0/1 | 1 | | | | |
| Merkel Cell Carcinoma | 1/2 | 1 | | | | Punctate Cy, Me |
| Neurofibroma | 0/13 | 13 | | | | |
| Nevus Sebaceous | 0/5 | 5 | | | | |
| Pilomatricoma | 0/1 | 1 | | | | |
| Poroma | 3/6 | 3 | 2 | 1 | | Me, Lu |
| Seborrheic Keratosis | 0/1 | 1 | | | | |
| Spiradenoma | 1/7 | 6 | 1 | | | Lu |
| Syringoma | 0/2 | 2 | | | | |
| Syringocystadenoma Papilliferum | 3/3 | | 1 | 2 | | Lu |
| Trichepithelioma | 0/10 | 10 | | | | |
| Urticaria Pigmentosa | 0/3 | 3 | | | | |
| Xanthogranuloma | 0/4 | 4 | | | | |
| Angiofibroma | 0/2 | 2 | | | | |
| Angiosarcoma | 0/2 | 2 | | | | |
| Glomangioma | 0/1 | 1 | | | | |
| Hemangiopericytome | 0/2 | 2 | | | | |
| Malignant Hemangiopericytoma | 0/1 | 1 | | | | |
| Blue Nevus | 0/5 | 5 | | | | |
| Spitz Nevus | 0/2 | 2 | | | | |
| Malignant Melanoma | 0/10 | 10 | | | | |

Abbreviations: Lu—Luminal portion of cell membrane; Me—Cell Membrane; Cy—Cytoplasm.

TABLE 6

Expression of Tumor-Associated Antigen CA6 in Salivary Gland Neoplasms as Immunohistochemically Detected by Monoclonal Antibody DS6

| Neoplasm | Reactive Cases/ Total Number of Cases | Nonreactive (Cases with <1% cells reactive) | 1+ (Cases with 1-9% cells reactive) | 2+ (Cases with 10-49% cells reactive) | 3+ (Cases with >50% cells reactive) | Major Patterns of CA6 Expression |
|---|---|---|---|---|---|---|
| Acinic Cell Carcinoma | 0/8 | 8 | | | | |
| Adenoid Cystic Carcinoma | 7/14 | 7 | 5 | 1 | 1 | Lu |
| Basal Cell Adenoma | 1/4 | 3 | 1 | | | Lu |
| Basal Cell Carcinoma | 0/1 | 1 | | | | |
| Clear Cell Carcinoma | 0/5 | 5 | | | | |
| Canalicular Adenoma | 0/1 | 1 | | | | |
| Malignant Mixed Tumor | 0/1 | 1 | | | | |
| Mucoepidermoid Carcinoma | 3/4 | 1 | | 3 | | Lu, Me |
| Pleomorphic Adenoma | 4/30 | 26 | 4 | | | Lu |
| Polymorphous Low Grade Carcinoma | 0/1 | 1 | | | | |
| Salivary Duct Carcinoma | 4/5 | 1 | | 2 | 2 | Lu, Me, Cy |
| Warthin Tumor | 2/16 | 14 | 2 | | | Lu |

Abbreviations: Lu—Luminal portion of cell membrane; Me—Cell Membrane; Cy—Cytoplasm.

TABLE 7

Non-Epithelial Neoplasms Which Do Not Express
Tumor-Associated Antigen CA6 as Studied Immunohistochemically
with Monoclonal Antibody DS6

| SITE | NEOPLASM | TOTAL CASES STUDIED |
|---|---|---|
| Adrenal | Neuroblastoma & Ganglioneuroblastoma | 21 |
| | Pheochromocytoma | 4 |
| Breast | Fibroadenoma | 1 |
| Brain | Glioblastoma Multiforme | 40 |
| | Anaplastic Astrocytoma | 5 |
| | Oligodendroglioma | 9 |
| | Pilocytic Astrocytoma | 12 |
| | Medulloblastoma | 10 |
| | Ependymoma | 15 |
| | Ganglion Cell Tumors | 4 |
| | Central Neurocytoma | 1 |
| | Schwannoma | 29 |
| | Hemanioblastoma | 6 |
| Gastro-intestinal | Appendiceal Carcinoid Tumor | 5 |
| | Appendiceal Adenocarcinoid | 1 |
| | Colonic Carcinoid Tumor | 5 |
| | Gastric Carcinoid | 6 |
| | GI Mesenchymal Tumors | 17 |
| Lung | Carcinoid Tumor | 21 |
| | Small Cell Carcinoma | 5 |
| | Large Cell Neuroendocrine Carcinoma | 6 |
| Lymphoma | Diffuse Small Cell Lymphomas | 31 |
| | Large Cell Lymphomas | 19 |
| | Follicular Lymphomas | 36 |
| | Blastic Lymphomas | 11 |
| | Hodgkins Disease | 29 |
| | Multiple Myeloma | 23 |
| | Langerhans Cell Histiocytosis | 8 |
| Leukemias | Acute Lymphoblastic Leukemia | 4 |
| | Acute Myelogenous Leukemia | 5 |
| | Chronic Myelogenous Leukemia | 5 |
| Oral Tissues | Ameloblastoma | 6 |
| Pancreas | Islet Cell Tumor | 6 |
| Parathyroid | Adenoma | 8 |
| Skin | Blue Nevus | 5 |
| | Spitz Nevus | 2 |
| Skin | Malignant Melanoma | 10 |
| | Dermatofibroma | 9 |
| | Dermatofibrosarcoma Protuberans | 4 |
| | Hemangioma | 8 |
| | Leiomyoma | 8 |
| | Leiomyosarcoma | 1 |
| | Neurofibroma | 13 |
| | Urticaria Pigmentosa Xanthogranuloma | 3 |
| | Xanthogranuloma | 4 |
| | Angiofibroma | 2 |
| | Angiosarcoma | 2 |
| | Glomangioma | 1 |
| | Hemangiopericytoma | 2 |
| | Malignant Hemangiopericytoma | 1 |
| Soft Tissue | Angiosarcoma | 1 |
| | Alveolar Soft Parts Sarcoma | 1 |
| | Chondrosarcoma | 2 |
| | Fibrosarcoma | 2 |
| | Granular Cell Tumor | 7 |
| | Hemangiopericytoma | 1 |
| | Leiomyosarcoma | 14 |
| | Liposarcoma | 4 |
| | Malignant Fibrous Histiocytoma | 6 |
| | Malignant Schwannoma | 6 |
| | Neurofibroma | 1 |
| | Osteosarcoma | 2 |
| | Rhabdomyosarcoma | 3 |
| | Undifferentiated Sarcoma | 2 |
| | Paraganglioma | 5 |
| | Primitive Neuroectodermal Tumor | 3 |
| Testicle | Choriocarcinoma | 4 |
| | Embryonal Carcinoma | 16 |
| | Seminoma | 18 |
| | Teratoma, Non-epithelial elements | 5 |
| | Yolk Sac Tumor | 12 |
| Thyroid | Medullary Carcinoma | 3 |

TABLE 8

Non-Epithelial Neoplasms Which Express Tumor-Associated Antigen CA6
as Detected Immunohistochemically by Monoclonal Antibody DS6

| Neoplasm | Reactive Cases/ Total Number of Cases | Nonreactive (Cases with <1% cells reactive) | 1+ (Cases with 1-9% cells reactive) | 2+ (Cases with 10-49% cells reactive) | 3+ (Cases with >50% cells reactive) | Major Patterns of CA6 Expression |
|---|---|---|---|---|---|---|
| Merkel Cell Carcinoma | 1/2 | 1 | | 1 | | Membranous & cytoplasmic |

TABLE 8-continued

Non-Epithelial Neoplasms Which Express Tumor-Associated Antigen CA6 as Detected Immunohistochemically by Monoclonal Antibody DS6

| Neoplasm | Reactive Cases/ Total Number of Cases | Nonreactive (Cases with <1% cells reactive) | 1+ (Cases with 1-9% cells reactive) | 2+ (Cases with 10-49% cells reactive) | 3+ (Cases with >50% cells reactive) | Major Patterns of CA6 Expression |
|---|---|---|---|---|---|---|
| Pituitary Adenoma | 2/21 | 19 | 2 | | | Luminal in pseudorosettes; punctate in cytoplasm |
| Small Intestinal Carcinoid Tumor | 1/9 | 8 | | 1 | | Luminal in rosettes |
| Synovial Sarcoma | 1/3 | 2 | | 1 | | Luminal and membranous |

The foregoing is illustrative of the present invention, and is not to be construed as limiting thereof. The invention is defined by the following claims, with equivalents of the claims to be included therein.

That which is claimed is:

1. A method of identifying a competing antibody selected from the group consisting of:
   (i) an antibody that specifically binds to the same epitope on a cell expressing a CA6 antigen that is bound by a monoclonal antibody produced by the hybridoma cell line DS6 deposited with the American Type Culture Collection as deposit number PTA-4449 or the same epitope on a CA6 antigen that is bound by a monoclonal antibody produced by the hybridoma cell line DS6 deposited with the American Type Culture Collection as deposit number PTA-4449, and
   (ii) an antigen-binding fragment of the antibody of (i) that specifically binds to the same epitope on a cell expressing a CA6 antigen that is bound by a monoclonal antibody produced by the hybridoma cell line DS6 deposited with the American Type Culture Collection as deposit number PTA-4449 or the same epitope on a CA6 antigen that is bound by a monoclonal antibody produced by the hybridoma cell line DS6 deposited with the American Type Culture Collection as deposit number PTA-4449, the method comprising:
   (a) contacting the antibody and labeled monoclonal antibody produced by the hybridoma cell line DS6 deposited with the American Type Culture Collection as deposit number PTA-4449 with a cell expressing a CA6 antigen containing an epitope specifically bound by a monoclonal antibody produced by the hybridoma cell line DS6 deposited with the American Type Culture Collection as deposit number PTA-4449 or with a CA6 antigen containing the same epitope bound by a monoclonal antibody produced by the hybridoma cell line DS6 deposited with the American Type Culture Collection as deposit number PTA-4449; and
   (b) determining if the antibody competes with the labeled monoclonal antibody produced by the hybridoma cell line DS6 deposited with the American Type Culture Collection as deposit number PTA-4449 for binding to the epitope on the cell expressing the CA6 antigen or to the epitope on the CA6 antigen.

2. The method of claim 1, wherein the competing antibody is a monoclonal antibody.

3. The method of claim 2, wherein the competing antibody is a chimeric antibody.

4. The method of claim 2, wherein the competing antibody is a humanized antibody.

5. The method of claim 2, wherein the method further comprises the step of chimerizing the competing antibody.

6. The method of claim 2, wherein the method further comprises the step of humanizing the competing antibody.

7. The method of claim 1, wherein the method further comprises the step of coupling the competing antibody to a therapeutic agent.

8. The method of claim 7, wherein the therapeutic agent is a radioisotope.

9. The method of claim 7, wherein the therapeutic agent is a cytotoxic agent.

10. The method of claim 7, wherein the therapeutic agent is a chemotherapeutic agent.

11. The method of claim 1, wherein the method further comprises the step of mixing the competing antibody with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,067,186 B2 | Page 1 of 1 |
| APPLICATION NO. | : 12/363191 | |
| DATED | : November 29, 2011 | |
| INVENTOR(S) | : Kellogg et al. | |

It is certified that error appears in the above-identified patent and that said Letters Patent is hereby corrected as shown below:

Column 7, Line 30: Please correct "agent is 3 the" to read -- agent is $^{131}$I, the --

Signed and Sealed this
Third Day of April, 2012

David J. Kappos
*Director of the United States Patent and Trademark Office*